United States Patent [19]

Ohashi et al.

[11] 4,420,554
[45] Dec. 13, 1983

[54] SILVER HALIDE PHOTOSENSITIVE MATERIALS

[75] Inventors: Minoru Ohashi; Kiyoshi Futaki; Katsuaki Iwaosa, all of Nagaokakyo, Japan

[73] Assignee: Mitsubishi Paper Mills, Ltd., Tokyo, Japan

[21] Appl. No.: 349,525

[22] Filed: Feb. 17, 1982

[30] Foreign Application Priority Data

Feb. 17, 1981 [JP] Japan .................................. 56-21764
Feb. 18, 1981 [JP] Japan .................................. 56-21425

[51] Int. Cl.³ .............................................. G03C 1/34
[52] U.S. Cl. ................................... 430/446; 430/445; 430/448; 430/955; 430/611; 430/613; 430/219; 430/957
[58] Field of Search .............. 430/434, 611, 613, 219, 430/614, 445, 446, 448, 955, 957

[56] References Cited

U.S. PATENT DOCUMENTS 2,981,624 4/1961 Dersch et al. .................... 430/611
3,674,478 7/1972 Grasshoff et al.
3,888,677 6/1975 Abele et al. ...................... 430/611
4,343,893 8/1982 Donald et al. .................... 430/611

FOREIGN PATENT DOCUMENTS 1209813 10/1970 United Kingdom ............... 430/611

Primary Examiner—Won H. Louie, Jr.
Attorney, Agent, or Firm—Cushman, Darby & Cushman

[57] ABSTRACT

There is disclosed a silver halide photosensitive material which contains in at least one of silver halide emulsion layers and colloid layers at least on antifoggant precursor compound represented by the general formula:

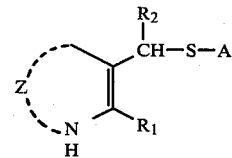

wherein A, Z, $R_1$ and $R_2$ are the same as defined previously. This photosensitive material is stabilized against overdevelopment fogging.

10 Claims, No Drawings

SILVER HALIDE PHOTOSENSITIVE MATERIALS

BACKGROUND OF THE INVENTION

This invention relates to a photosensitive material comprising a silver halide emulsion layer stabilized against over-development fogging.

When a silver halide photosensitive material is subjected to developing treatment under severe conditions such as development at comparatively high temperatures or rapid development in a short period of time by the use of a highly active developer (a developer at a high temperature and a high pH), there is a danger of the accompanied reduction of silver halide grains containing entirely no latent image nuclei. The fog produced under the said conditions by the undesired reduction of unexposed silver halide grains manifests itself especially intensely at the end of common development processing and is called over-development fog.

The antifoggants known to be effective in reducing the over-development fog include mercury compounds and heterocyclic mercapto compounds. Although these antifoggants generally reduce the fogging during the course of development or in case of over development, yet, when used in an amount sufficient for the reduction of above-said fogging, they have also a disadvantage of appreciably decreasing the sensitivity of silver halide photosensitive materials. A basic disadvantage of the direct incorporation of heterocyclic mercapto compounds or others which are generally active by themselves against the over-development fogging into a silver halide emulsion originates in the fact that they are active to full extent from the instant of incorporation, that is, they remain active throughout the manufacturing step, shelf period, and the development step; as a consequence they exhibit an undesirable desensitizing effect on the photosensitive material during the manufacture and shelf period thereof.

In order to solve the above problem, attempts have heretofore been made in the art to protect the mercapto group of the aforementioned compounds with a hydrolyzable group, thus rendering the compound inactive during the period wherein its activity is undesirable (throughout the entire period prior to the development processing, including the manufacturing step), and to reactivate the compound by alkaline hydrolysis in the development step. Such substituent groups are generally moieties of thioesters or thioethers of the aforementioned mercapto-type antifoggants.

Regarding the thioester-type substituent, those of the carboxylic acids, sulfonic acids, and carbonic acid derivatives are disclosed in many patents such as, for example, German Pat. No. 1,597,503, U.S. Pat. No. 3,260,597 and German Patent Application "Offenlegungsschrift" No. 2,061,972. Although hydrolyzable in an alkaline developer medium, these thioesters have a disadvantage of being gradually hydrolyzed at least partially also in neutral or weakly acid region. As a consequence, although can be added in inactive form into the emulsion, these thioester-type antifoggants tend to cause undesirable desensitization owing to the partial hydrolysis in the step of emulsion making or during storage of the photosensitive material, if the time span is sufficiently extended.

As contrasted, although the antifoggants having thioether-type substituents, such as, for example, those disclosed in U.S. Pat. Nos. 2,981,624 and 3,260,597 and German Pat. No. 1,173,796 are indeed completely stable in a neutral or weakly acid medium, yet they are unable to prevent effectively the over-development fogging from occurring, because in the development step they are either unable to regenerate the original mercapto-antifoggant or able to regenerate but very slowly.

Further, those compounds disclosed in U.S. Pat. No. 3,674,478 which are able to release a quinone-methide or naphthoquinone-methide and a mercapto-antifoggant in the presence of alkali are indeed able to release quickly the antifoggant in the presence of alkali, but are disadvantageous in that in a weakly acid medium they are unstable to some degree, gradually releasing the antifoggant. As a consequence, if the time interval between the preparation and coating of an emulsion (having a pH in the weakly acid region) is sufficiently long, the antifoggant will be entirely released into the emulsion, causing undesirable desensitization.

SUMMARY OF THE INVENTION

A primary object of this invention, therefore, is to provide an antifoggant (hereinafter referred to as antifoggant precursor) having an inactivated mercapto group which is completely stable in the neutral or weakly acid pH region but is capable of releasing an antifoggant of a predetermined activity in the alkaline pH range (during the developing treatment).

As a result of extensive studies, the present inventors have found that a thioether-type antifoggant precursor represented by the general formula (I) achieves the above-said object of this invention:

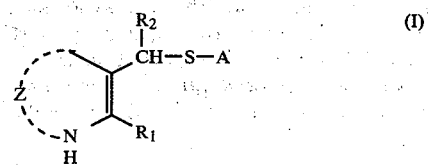

wherein A represents the heterocyclic group of a mercapto-antifoggant; Z represents a diacyl group of the formula

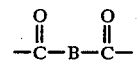

or an atomic group necessary to form an indole ring; $R_1$ represents a hydrogen atom, alkyl group, phenyl group, carboxyl group or alkoxycarbonyl group; $R_2$ represents a hydrogen atom, alkyl group or phenyl group; B represents a methylene group of the formula

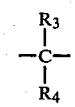

or an amino group of the formula

$R_3$, $R_4$ and $R_5$ each represents a hydrogen atom or alkyl group; and the positions from 4 to 7 of the indole ring may be substituted with a halogen atom, alkyl group, phenyl group, alkoxy group, hydroxyl group, nitro group, carboxyl group or alkoxycarbonyl group.

DESCRIPTION OF PREFERRED EMBODIMENT

A particularly preferable group of the present antifoggant precursors is represented by the general formula (II):

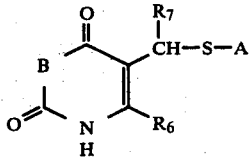
(II)

wherein A represents a heterocyclic group of the mercapto-antifoggant; B represents a methylene group of the formula

or an amino group of the formula

$R_6$ and $R_7$ each represents a hydrogen atom, alkyl group (preferably an alkyl group having 1 to 5 carbon atoms), or phenyl group, and $R_3$, $R_4$ and $R_5$ each represents a hydrogen atom or alkyl group (preferably an alkyl group having 1 to 10 carbon atoms).

Another preferable group of the present antifoggant precursors is represented by the general formula (III):

(III)

wherein A represents a heterocyclic group of the mercapto-antifoggant; $R_8$, $R_9$, $R_{10}$ and $R_{11}$ each represents a hydrogen atom, halogen atom, alkyl group (preferably an alkyl group having 1 to 10 carbon atoms), phenyl group, alkoxy group (preferably an alkoxy group having 1 to 5 carbon atoms), hydroxyl group, nitro group, carboxyl group, or alkoxycarbonyl group; the alkyl group, alkoxy group or alkoxycarbonyl group represented by $R_8$ to $R_{11}$ may form a ring; $R_{12}$ represents a hydrogen atom, alkyl group (preferably an alkyl group having 1 to 10 carbon atoms), phenyl group, carboxyl group, or alkoxycarbonyl group; and $R_{13}$ represents a hydrogen atom, alkyl group (preferably an alkyl group having 1 to 10 carbon atoms), or phenyl group.

When added to the photographic colloid layer, the compounds of formula (II) remain stable without crystallizing out and the stability of the emulsion does not change with time.

Although the aforementioned mercapto-antifoggant may be any of the compounds having an antifogging activity, particularly preferred are 5- or 6-membered nitrogen-containing heterocyclic compounds having a sulfur atom bonded to the carbon atom adjacent to the nuclear nitrogen atom. As examples of typical hetero rings, mention may be made of tetrazole ring, 1,2,4-triazole ring, benzoxazole ring, benzothiazole ring, benzoimidazole ring, pyridine ring, and pyrimidine ring.

Below are given examples of typical antifoggant precursors represented by the general formula (I), but the invention is not limited thereto.

| Compound No. |
| --- |
| 1. 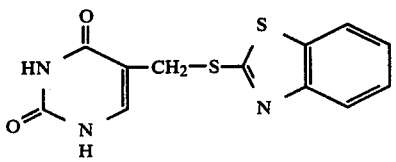 |
| 2. 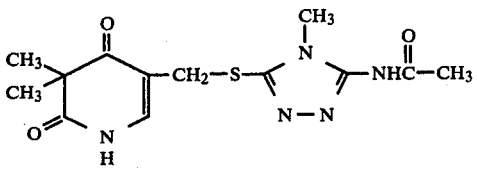 |
| 3. 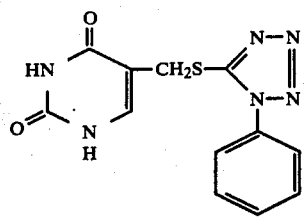 |

-continued
| Compound No. | |
|---|---|
| 4. | 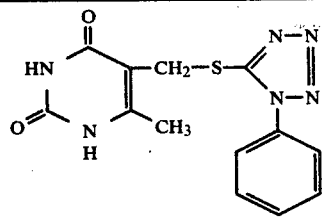 |
| 5. | 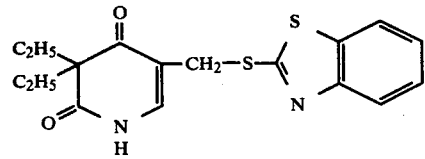 |
| 6. | 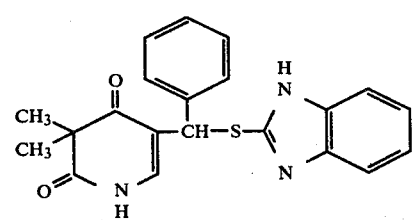 |
| 7. | 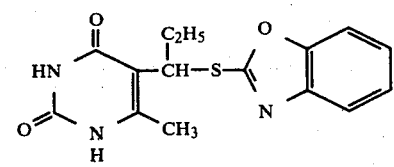 |
| 8. | 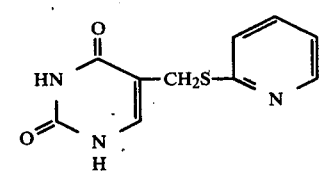 |
| 9. | 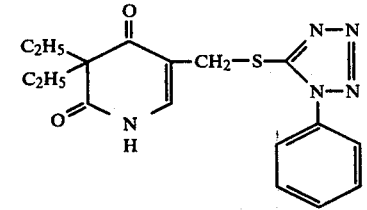 |
| 10. | 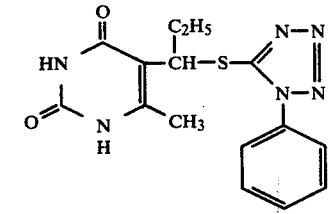 |
| 11. | 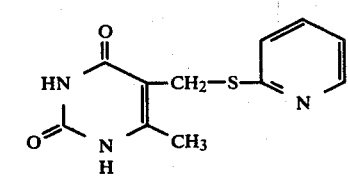 |

| Compound No. | |
|---|---|
| 12. | 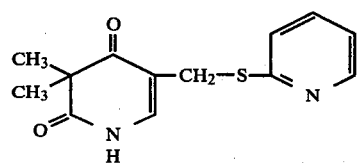 |
| 13. | 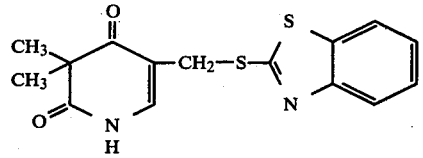 |
| 14. | 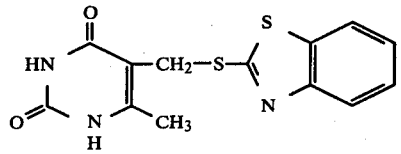 |
| 15. | 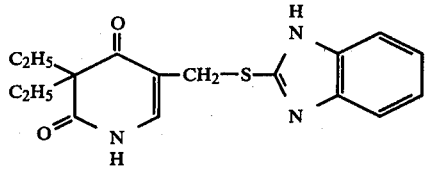 |
| 16. | 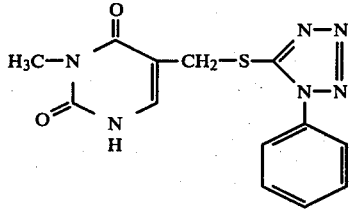 |
| 17. | 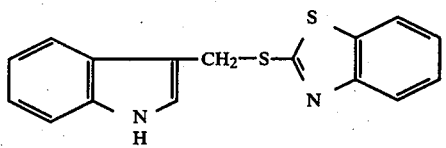 |
| 18. | 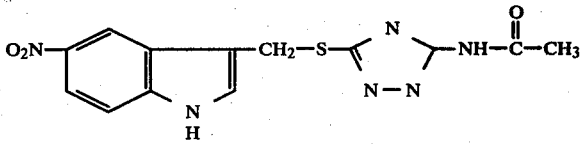 |
| 19. | 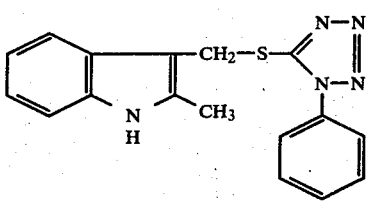 |

-continued
| Compound No. | |
|---|---|
| 20. | 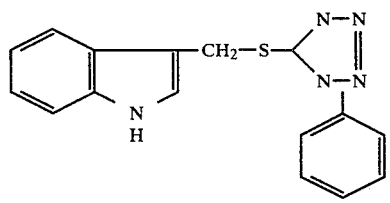 |
| 21. | 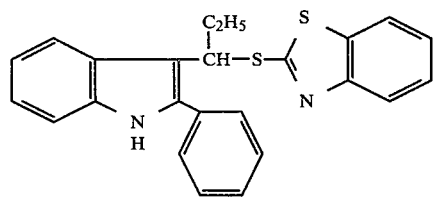 |
| 22. | 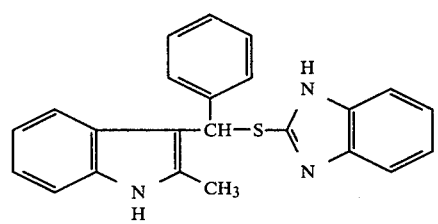 |
| 23. | 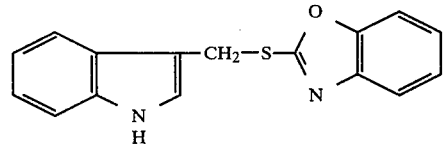 |
| 24. | 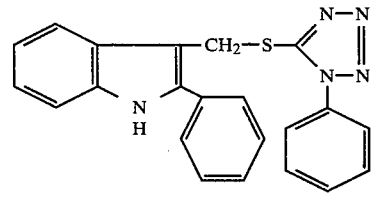 |
| 25. | 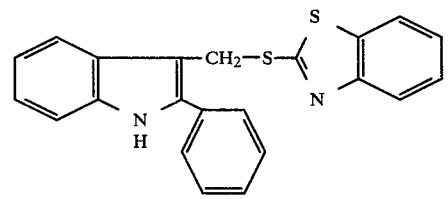 |
| 26. | 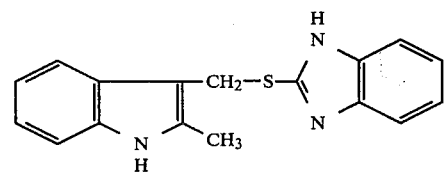 |
| 27. | 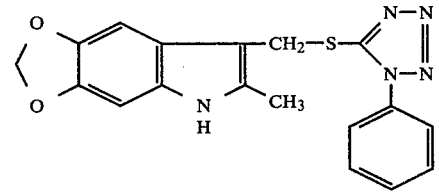 |

-continued
| Compound No. | |
|---|---|
| 28. | 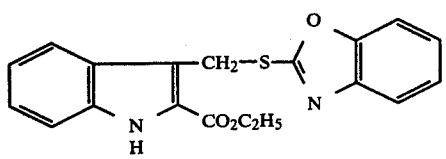 |
| 29. | 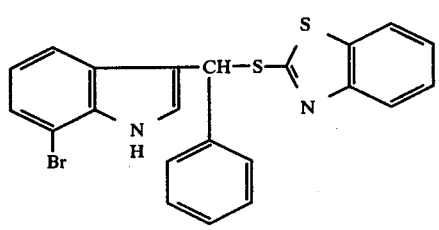 |
| 30. | 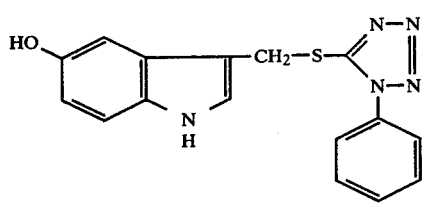 |
| 31. | 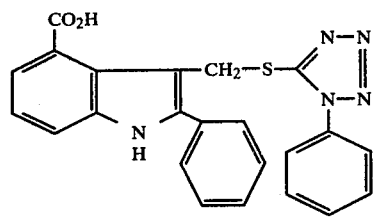 |
| 32. | 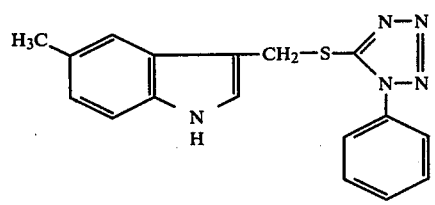 |
| 33. | 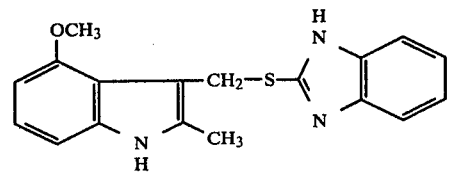 |
| 34. | 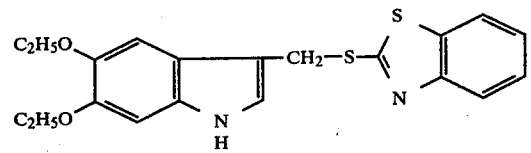 |
| 35. | 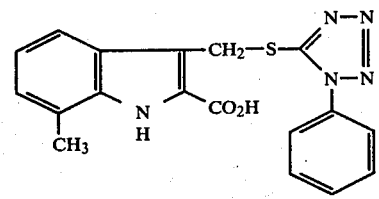 |

As is apparent from the synthesis Examples given below, the compounds of this invention represented by the general formula (I) are readily obtained by the reaction of a corresponding mercapto-antifoggant with a hydroxymethyl compound represented by the general formula (IV), shown below, in the presence of an acid such as, for example, hydrochloric acid, sulfuric acid, acetic acid, etc., according to the reaction scheme (a) or by the reaction of a sulfide represented by the general formula (V), shown below, with an indole compound in the presence of an acid such as, for example, hydrochloric acid or sulfuric acid, according to the reaction scheme (b).

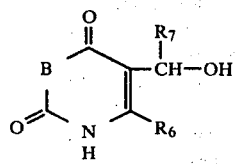

(IV)

Reaction scheme (a)

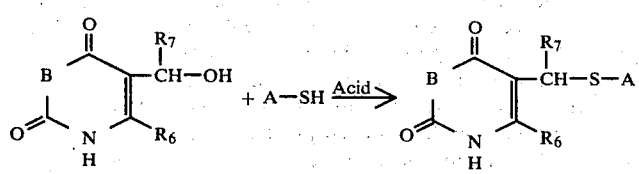

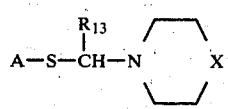

(V)

Reaction scheme (b)

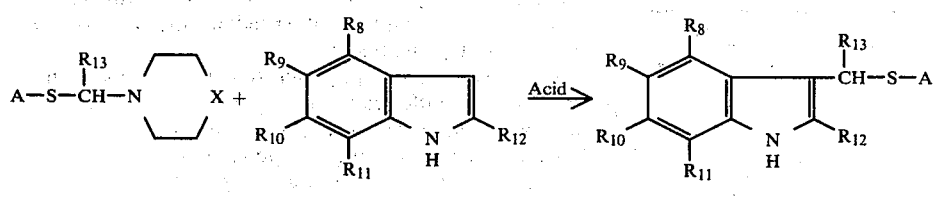

wherein A, B, and $R_6$ to $R_{13}$ are as defined before and X represents an oxygen atom or methylene group.

The compounds represented by the general formula (IV) are easily synthesized by referring to or applying the methods described, for example, in J. Am. Chem. Soc., 31, 2521-2527 (1950) and 32, 991-994 (1960); Helv. Chim. Acta, 37, 1854 (1954).

The compounds represented by the general formula (V) are easily prepared by the reaction of the corresponding mercapto-antifoggant (A-SH) with an aldehyde, $R_{13}$—CH=O, and a secondary amine,

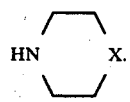

Examples of synthesis of the present antifoggant precursors are shown below.

Synthesis Example 1 (Synthesis of compound No. 3)

A solution was obtained by heating together 14.2 g of 5-hydroxymethyluracil, 18.0 g of 1-phenyl-5-mercaptotetrazole, 100 ml of dioxane, and 40 ml of water. The solution was admixed with 1 ml of concentrated hydrochloric acid and refluxed for about 2 hours. After cooling, the precipitated crystals were collected by filtration and recrystallized from aqueous dioxane. Yield: 21.6 g; melting point: 222°-223° C.

Elementary analysis:

|  | C % | H % | N % |
|---|---|---|---|
| Calculated | 47.67 | 3.33 | 27.80 |
| Found | 47.65 | 3.28 | 27.92 |

Synthesis Example 2 (Synthesis of compound No. 9).

To a solution of 9.9 g of 5-hydroxymethylpyridyld-ione and 9.0 g of 1-phenyl-5-mercaptotetrazole in 80 ml of dioxane, was added 0.5 ml of concentrated hydrochloric acid. The mixture was heated under reflux for about 1.5 hours. The reaction mixture was poured into about 300 ml of ice-water and extracted with ethyl acetate. The organic layer was washed with water and dried over anhydrous sodium sulfate. After removal of sodium sulfate by filtration, the ethyl acetate layer was freed from the solvent by distillation under reduced pressure. The residue was recrystallized from an ethyl acetate-cyclohexane mixture to obtain the compound No. 9 Yield: 15.9 g; melting point: 121°-122° C.

Elementary analysis:

|  | C % | H % | N % |
|---|---|---|---|
| Calculated | 57.12 | 5.36 | 19.60 |
| Found | 57.10 | 5.28 | 19.47 |

Synthesis Example 3 (Synthesis of compound No. 19)

(i) Synthesis of the intermediate, piperidinomethyl (1-phenyltetrazol-5-yl) sulfide.

To a solution of 53.5 g of 1-phenyl-5-mercaptotetrazole in 300 ml of ethanol, which had been cooled below 20° C., was added dropwise with stirring 25.5 g of piperidine. To the mixture was then added 25.7 ml of 35-% formalin and the resulting mixture was heated with stirring at 70° C. for about one hour. The reaction mixture was freed from the solvent by distillation under reduced pressure and the residue was recrystallized from ligroin. Yield: 66.3 g; melting point: 138°–139.5° C. Elementary analysis:

|  | C % | H % | N % |
|---|---|---|---|
| Calculated | 56.70 | 6.22 | 25.43 |
| Found | 56.73 | 6.20 | 25.45 |

(ii) Synthesis of compound No. 19

A solution was prepared by heating 13.2 g of 2-methylindole, 28.3 g of piperidinomethyl(1-phenyltetrazol-5-yl)sulfide obtained in (i) above, and 200 ml of dioxane. To the solution was added 8.6 ml of concentrated hydrochloric acid. The mixture was refluxed for about one hour and the precipitated crystals were removed by filtration. The filtrate was poured into about one liter of water and extracted with ethyl acetate. The organic layer was washed with water and dried over anhydrous sodium sulfate. After removal of sodium sulfate by filtration, the filtrate was stripped of the solvent by distillation under reduced pressure, and the residue was recrystallized from aqueous methanol. Yield: 30.6 g; melting point: 127°–128.5° C. Elementary analysis:

|  | C % | H % | N % |
|---|---|---|---|
| Calculated | 63.53 | 4.70 | 21.79 |
| Found | 63.70 | 4.59 | 21.83 |

EXAMPLE 4

(Synthesis of compound No. 24)

(i) Synthesis of the intermediate, morpholinomethyl(1-phenyltetrazol-5-yl) sulfide.

The preparative procedure was the same as in (i) of Synthesis Example 3, except that 26.1 g of morpholine was used in place of the piperidine. The crude crystals were recrystallized from ethyl acetate.

Yield: 72.0 g; melting point: 161°–162° C. Elementary analysis:

|  | C % | H % | N % |
|---|---|---|---|
| Calculated | 51.96 | 5.45 | 25.25 |
| Found | 51.94 | 5.51 | 25.14 |

(ii) Synthesis of Compound No. 24

Into 100 ml of dioxane, were dissolved with heating 9.65 g of 2-phenylindole and 14.2 g of morpholinomethyl(1-phenyltetrazol-5-yl)sulfide prepared in (i) above. After adding 4.2 ml of concentrated hydrochloric acid, the mixture was heated under reflux for about one hour. After cooling, the precipitated crystals were removed by filtration and the filtrate was concentrated under reduced pressure and recrystallized from aqueous methanol. Yield: 16.3 g; melting point: 153°–153.5° C. Elementary analysis:

|  | C % | H % | N % |
|---|---|---|---|
| Calculated | 68.90 | 4.47 | 18.27 |
| Found | 68.84 | 4.39 | 18.29 |

According to this invention, the present antifoggant precursor is incorporated in the silver halide emulsion layer of the photosensitive material or in those colloid layers, such as layers of overcoating or undercoating to the emulsion layer, which are permeable to water through to or out from said emulsion layer. The incorporation of the present antifoggant precursor in the emulsion layer or said colloid layer can be effected by dissolving the antifoggant precursor in a water-miscible solvent such as, for example, DMF, methanol or ethanol and admixing, before coating, into a silver halide emulsion or a colloidal dispersion to be used for said colloid layer. It is also possible to disperse the antifoggant precursor with a latex by means of a technique disclosed in Japanese Patent Application "Kokai" (Laid-open) No. 137,131/78 and admix the dispersion in the silver halide emulsion or the colloid dispersion. The solution or dispersion of the present antifoggant precursor can be incorporated in the silver halide emulsion in any stage of manufacture, but it is preferable to add to the silver halide emulsion just before coating.

The suitable concentration of the present antifoggant precursor varies depending upon the type of compound and its location within the photographic material. In incorporating into the silver halide emulsion, it is added in an amount of 0.1 to 100 millimoles, preferably 0.5 to 50 millimoles for 1 mole of silver halide, whereas it is added in somewhat larger amounts in incorporating into other colloid layers which are in contact with or become in contact with the silver halide emulsion layer in the developing treatment.

After exposure the photosensitive material containing the present antifoggant precursor is developed with common developers. The developed material is stabilized in a common fixing or stabilizing bath.

The present invention is adaptable for any type of silver halide emulsions such as, for example, spectrally sensitized or nonsensitized emulsions, X-ray emulsions, infra red-sensitive emulsions as well as high-sensitivity negative emulsions, low-sensitivity positive emulsions, orthochromatic emulsions, or panchromatic emulsions. The photosensitive silver salt may be of any type such as, for example, silver bromide, silver iodide, silver chloride, mixed halide of silver (e.g. silver chlorobromide and silver iodobromide). The silver halide may be dispersed in common hydrophilic colloids such as, for example, gelatin, casein, polyvinyl alcohol and carboxymethylcellulose, gelatin being most advantageous. The silver halide emulsion may be sensitized either chemically or optically. The chemical sensitization is effected by the ripening in the presence of a small amount of a sulfur-containing compound (e.g. allyl thiocyanate, allyl thiourea or sodium thiosulfate). Further, the emulsion can be sensitized with a reducing agent (for example, a tin compound described in French Pat. No. 1,146,955 and U.S. Pat. No. 2,487,850; an iminoaminomethanesulfinic acid compound described in Brit. Pat. No. 789,823) and a small amount of noble metals (for example, gold, platinum, palladium, iridium, ruthenium and rhodium). Further, the emulsion may be sensitized with cyanine and merocyanine dyes.

Other additives such as, for example, development accelerators, sensitizers and antioxidants may be included in the silver halide emulsion layers or other water-permeable colloid layers. Further, the present antifoggant precursors may be used in combination with other antifoggant precursors.

The invention is illustrated below in detail with reference to Examples.

EXAMPLE 1

A silver iodochlorobromide gelatin emulsion of 0.45 μm in average grain size comprising 65.5 mole-% of silver bromide, 34.0 mole-% of silver chloride and 0.5 mole-% of silver iodide was prepared by the neutral single jet process. After physical ripening and subsequent desalting by washing with water, gelatin was added to the emulsion. Then chemical sensitization was effected by adding sodium thiosulfate. The emulsion was finished by adding a sensitizing dye, a stabilizer, a surface active agent, and a hardener. The resulting gelatin silver halide emulsion was divided into 13 portions. To 7 portions were added independently the compounds described above as examples of present antifoggant precursors each in an amount of 2 millimoles for 1 mole of silver halide. To three of the remaining portions, was added 1-phenyl-5-mercaptotetrazole, 2-mercaptobenzothiazole, or 2-mercaptobenzimidazole in an amount of 2 millimoles for each mole of silver halide (Reference A). To two other portions were added the thioethers represented by the following formulas in an amount of 2 millimoles for each mole of silver halide.

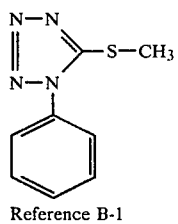
Reference B-1

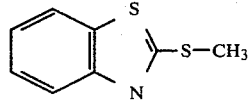
Reference B-2

None was added to the last portion (Reference C).

The 13 emulsions thus obtained were independently coated on polyethylene-coated photographic base paper sheets at a coverage of 2.5 g in terms of silver nitrate and 6.0 g of gelatin per square meter, and dried. The test pieces thus prepared were divided into two groups. The one group was heated at 40° C. for 5 days, while the other was heated for 5 days at 50° C. and 80% relative humidity. A portion of each test piece was exposed through a step optical wedge, developed in a developer of the composition given below, at 20° C. for 120 seconds, then passed through a stopper bath and a fixing bath, washed with water, dried, and tested for photographic characteristics.

Developer:

| | |
|---|---|
| Water | 750 ml |
| Metol | 1.0 g |
| Hydroquinone | 4.0 g |
| Sodium sulfite | 15.0 g |
| Sodium carbonate monohydrate | 26.7 g |
| Potassium bromide | 0.7 g |
| Water to make up to | 1,000 ml |

The unexposed portion of each test piece was also treated in the same developer at 20° C. for 10 minutes to examine the fogging. The results obtained were as shown in Table 1.

TABLE 1

| Sample No. | Antifoggant precursor (Compound No.) | 40° C., 5 days | | | | 50° C., 80% RH, 5 days | | | |
|---|---|---|---|---|---|---|---|---|---|
| | | Sensitivity ratio | γ | Max. density | Fog | Sensitivity ratio | γ | Max. density | Fog |
| 1 | 3 | 130.5 | 3.20 | 2.30 | 0.05 | 129.8 | 3.15 | 2.15 | 0.05 |
| 2 | 4 | 130.6 | 3.03 | 2.25 | 0.06 | 130.0 | 3.00 | 2.20 | 0.05 |
| 3 | 9 | 132.6 | 3.20 | 2.21 | 0.05 | 131.0 | 3.05 | 2.11 | 0.05 |
| 4 | 1 | 130.0 | 3.30 | 2.30 | 0.05 | 125.3 | 3.21 | 2.20 | 0.04 |
| 5 | 5 | 132.0 | 2.95 | 2.20 | 0.06 | 131.1 | 2.90 | 2.00 | 0.05 |
| 6 | 14 | 129.0 | 3.00 | 2.30 | 0.05 | 128.0 | 2.95 | 2.15 | 0.05 |
| 7 | 15 | 128.5 | 3.05 | 2.26 | 0.04 | 127.9 | 3.01 | 2.09 | 0.04 |
| Reference A-1 | 1-Phenyl-5-mercaptotetrazole | 100.0 | 2.3 | 2.15 | 0.04 | 95.0 | 2.73 | 2.00 | 0.03 |
| A-2 | 2-Mercaptobenzothiazole | 93.5 | 2.7 | 2.0 | 0.04 | 93.8 | 2.67 | 2.05 | 0.03 |
| A-3 | 2-Mercaptobenzoimidazole | 96.0 | 2.65 | 2.0 | 0.03 | 94.5 | 2.60 | 2.05 | 0.04 |
| B-1 | Reference B-1 | 133.0 | 3.0 | 2.30 | 0.27 | 135.5 | 2.96 | 2.21 | 0.23 |
| B-2 | Reference B-2 | 133.5 | 2.9 | 2.25 | 0.25 | 134.0 | 2.98 | 2.25 | 0.26 |
| C | None | 135.0 | 3.0 | 2.30 | 0.23 | 136.0 | 2.80 | 2.18 | 0.29 |

As is apparent from Table 1, it is seen that the present compound showed very little decrease in maximum density and in contrast (γ value), indicating no adverse effect on photographic characteristics. Since the photographic characteristics were not substantially changed with the change in heating conditions, it is understood that the present antifoggant precursor has undergone no partial hydrolysis during storage. Further, as compared with References B and C, the emulsion containing the present antifoggant precursor showed a fog level as low as that of Reference A, indicating that it had been efficiently hydrolyzed in the developer, releasing the corresponding antifoggant. Moreover, as is apparent from the data on the sensitivity ratio [a relative value of sensitivity as compared with the sensitivity (assumed to be 100.0) of Reference A-1 heated at 40° C. for 5 days], the antifoggant precursor of this invention causes no undesirable decline in sensitivity as compared with References A-1, A-2 and A-3.

EXAMPLE 2

A silver iodochlorobromide gelatin emulsion prepared as in Example 1 was chemically sensitized and finished up by adding thereto a sensitizing dye, stabilizer, surface active agent, and hardener. The resulting gelatin silver halide emulsion was divided into 6 portions. To three of them were added respectively the compounds mentioned previously as examples of antifoggant precursors, each in an amount of 2 millimoles per mole of silver halide. For comparison, one of the remaining three portions of emulsion was incorporated with 1-phenyl-5-mercaptotetrazole (Reference A) and another portion with the following antifoggant precursor disclosed in U.S. Pat. No. 3,674,478, each in an amount of 2 millimoles per mole of silver halide:

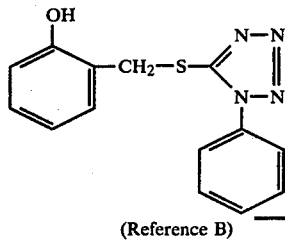

(Reference B)

The last portion of emulsion was used as such without any further additive (Reference C). The antifoggant precursors or antifoggants were added to the emulsion just before coating. In order to test the storage stability of the emulsion containing the antifoggant or antifoggant precursor, the remainder of each emulsion after coating was kept at 40° C. and coated on a base sheet at predetermined time intervals. The coating of the emulsion was performed in the same manner as in Example 1. Each coated test piece was kept at 40° C. for 5 days and examined for photographic characteristics and fog density as in Example 1. The results obtained were as shown in Table 2.

TABLE 2

| | | Storage stability of emulsion | | | | | |
|---|---|---|---|---|---|---|---|
| | | Coated immediately after addition | | Coated after 1 hour | | Coated after 4 hours | |
| Sample No. | Antifoggant precursor (Compound No.) | Sensitivity ratio | Fog | Sensitivity ratio | Fog | Sensitivity ratio | Fog |
| 1 | 3 | 131.4 | 0.05 | 131.0 | 0.05 | 130.8 | 0.05 |
| 2 | 4 | 132.1 | 0.06 | 131.8 | 0.05 | 131.7 | 0.05 |
| 3 | 9 | 129.8 | 0.05 | 129.0 | 0.05 | 129.0 | 0.05 |
| 4 | Reference A | 100.0 | 0.04 | 99.8 | 0.04 | 99.6 | 0.04 |
| 5 | B | 130.0 | 0.07 | 120.5 | 0.06 | 108.3 | 0.05 |
| 6 | C | 135.0 | 0.27 | 136.5 | 0.28 | 138.0 | 0.29 |

Note:
Sensitivity ratio: A relative value of sensitivity as compared with the sensitivity (assumed to be 100.0) of Reference A-1 coated immediately after the addition of antifoggant.

As is apparent from Table 2, the antifoggant precursor of this invention is also excellent in storage stability of the emulsion (stability of the emulsion as a function of time) containing it.

EXAMPLE 3

Test were performed in a manner similar to that in Example 1, using other antifoggant precursors. The results obtained were as shown in Table 3.

TABLE 3

| | | 40° C., 5 days | | | | 50° C., 80% RH, 5 days | | | |
|---|---|---|---|---|---|---|---|---|---|
| Sample No. | Antifoggant precursor (Compound No.) | Sensitivity ratio | γ | Max. density | Fog | Sensitivity ratio | γ | Max. density | Fog |
| 1 | 19 | 133.0 | 2.95 | 2.25 | 0.06 | 132.0 | 2.90 | 2.20 | 0.05 |
| 2 | 20 | 132.5 | 3.05 | 2.30 | 0.07 | 132.1 | 3.01 | 2.21 | 0.06 |
| 3 | 24 | 133.1 | 3.20 | 2.30 | 0.06 | 132.4 | 3.11 | 2.20 | 0.06 |
| 4 | 17 | 130.0 | 3.20 | 2.26 | 0.06 | 129.1 | 3.10 | 2.17 | 0.05 |
| 5 | 25 | 130.5 | 3.30 | 2.25 | 0.05 | 130.0 | 3.18 | 2.18 | 0.06 |
| 6 | 26 | 129.5 | 3.00 | 2.21 | 0.06 | 129.2 | 2.91 | 2.20 | 0.06 |
| Reference C | None | 136.0 | 3.0 | 2.30 | 0.29 | 137.0 | 2.81 | 2.18 | 0.29 |

Example 4

Tests were performed in a manner similar to that in Example 2, using other antifoggant precursors. The results obtained were as shown in Table 4.

TABLE 4

| | | Storage stability of emulsion | | | | | |
|---|---|---|---|---|---|---|---|
| | | Coated immediately after addition | | Coated after one hour | | Coated after 4 hours | |
| Sample No. | Antifoggant precursor (Compound No.) | Sensitivity ratio | Fog | Sensitivity ratio | Fog | Sensitivity ratio | Fog |
| 1 | 19 | 133.0 | 0.06 | 132.1 | 0.05 | 131.9 | 0.05 |
| 2 | 20 | 132.5 | 0.07 | 131.8 | 0.06 | 131.5 | 0.06 |
| 3 | 24 | 133.1 | 0.06 | 132.0 | 0.06 | 131.3 | 0.05 |
| 4 | Reference A | 100.0 | 0.04 | 99.8 | 0.04 | 99.6 | 0.04 |
| 5 | B | 130.0 | 0.07 | 120.5 | 0.06 | 108.3 | 0.05 |

TABLE 4-continued

| | | Storage stability of emulsion | | | | | |
|---|---|---|---|---|---|---|---|
| | | Coated immediately after addition | | Coated after one hour | | Coated after 4 hours | |
| Sample No. | Antifoggant precursor (Compound No.) | Sensitivity ratio | Fog | Sensitivity ratio | Fog | Sensitivity ratio | Fog |
| 6 | C | 135.0 | 0.28 | 136.5 | 0.28 | 138.0 | 0.29 |

As is apparent from Table 4, the antifoggant precursor of this invention is also excellent in storage stability of the emulsion containing it.

What is claimed is:

1. In a silver halide photographic photosensitive material which comprises a support and photographic layers provided thereon, the improvement which comprises including in at least one of silver halide emulsion layers and colloid layers permeable to water through to or out from said emulsion layer at least one development fog inhibiting compound represented by the following general formula (I):

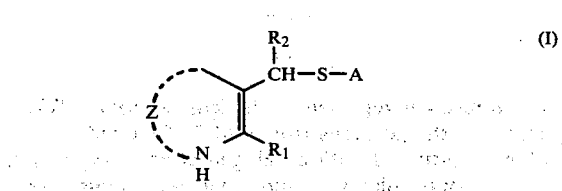

wherein A represents the heterocyclic group of a mercapto-antifoggant; Z represents a diacyl group of the formula

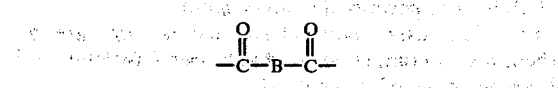

or an atomic group necessary to form an indole ring; $R_1$ represents a hydrogen atom, alkyl group, phenyl group, carboxyl group or alkoxycarbonyl group; $R_2$ represents a hydrogen atom, alkyl group or phenyl group; B represents a methylene group of the formula

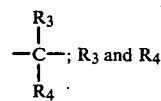

each represents a hydrogen atom or alkyl group; and the positions from 4 to 7 of the indole ring may be substituted with a halogen atom, alkyl group, phenyl group, alkoxy group, hydroxyl group, nitro group, carboxyl group or alkoxycarbonyl group.

2. A photosensitive material according to claim 1, wherein said development fog inhibiting compound is represented by the following general formula (II):

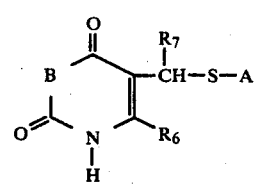

wherein A represents a heterocyclic group of the mercapto-antifoggant; B represents a methylene group of formula

$R_6$ and $R_7$ each represents a hydrogen atom, alkyl group, or phenyl group, and $R_3$, and $R_4$ each represents a hydrogen atom or alkyl group.

3. A photosensitive material according to claim 2, wherein $R_3$ and $R_4$ represent alkyl group of 1 to 10 carbon atoms.

4. A photosensitive material according to claim 1, wherein said development fog inhibiting compound is represented by the following general formula (III):

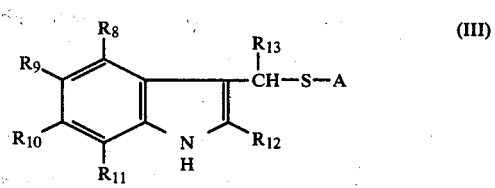

wherein A represents a heterocyclic group of the mercapto-antifoggant; $R_8$, $R_9$, $R_{10}$ and $R_{11}$ each represents a hydrogen atom, halogen atom, alkyl group, phenyl group, alkoxy group, hydroxyl group, nitro group, carboxyl group, or alkoxycarbonyl group; the alkyl group, alkoxy group or alkoxycarbonyl group represented by $R_8$ to $R_{11}$ may form a ring; $R_{12}$ represents a hydrogen atom, alkyl group, phenyl group, carboxyl group, or alkoxycarbonyl group; and $R_{13}$ represents a hydrogen atom, alkyl group or phenyl group.

5. A photosensitive material according to claim 4, wherein $R_{12}$ is an alkyl group of 1 to 5 carbon atoms or phenyl group.

6. A photosensitive material according to claim 1, wherein $R_2$ is hydrogen atom.

7. A silver halide emulsion which contains at least one development fog inhibiting compound represented by the following general formula (I):

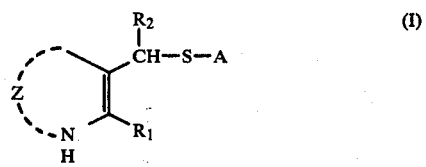

wherein A represents the heterocyclic group of a mercaptoantifoggant; Z represents a diacyl group of the formula

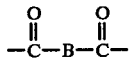

or an atomic group necessary to form an indole ring; $R_1$ represents a hydrogen atom, alkyl group, phenyl group, carboxyl group or alkoxycarbonyl group; $R_2$ represents a hydrogen atom, alkyl group or phenyl group; B represents a methylene group of the formula

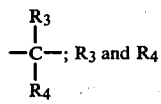

each represents a hydrogen atom or alkyl group; and the positions from 4 to 7 of the indole ring may be substituted with a halogen atom, alkyl group, phenyl group, alkoxy group, hydroxyl group, nitro group, carboxyl group or alkoxycarbonyl group.

8. A process for forming images which comprises exposing in an imagewise manner a silver halide photographic photosensitive material which contains in at least one of silver halide emulsion layers and colloid layers permeable to water through to or out from said emulsion layer at least one development fog inhibiting compound represented by the following general formula (I):

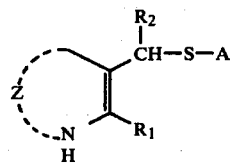

wherein A represents the heterocyclic group of a mercapto-antifoggant; Z represents a diacyl group of the formula

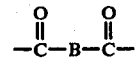

or an atomic group necessary to form an indole ring; $R_1$ represents a hydrogen atom, alkyl group, phenyl group, carboxyl group or alkoxycarbonyl group; $R_2$ represents a hydrogen atom, alkyl group or phenyl group; B represents a methylene group of the formula

$R_3$ and $R_4$ each represents a hydrogen atom or alkyl group; and the positions from 4 to 7 of the indole ring may be substituted with a halogen atom, alkyl group, phenyl group, alkoxy group, hydroxyl group, nitro group, carboxyl group or alkoxycarbonyl group and then developing the exposed photosensitive material.

9. A photosensitive material according to claim 1 wherein said compound is added in an amount of 0.1 to 100 millimole per mole of silver halide.

10. A photosensitive material according to claim 9 wherein said compound is added in an 0.5 to 50 millimoles per mole of silver halide.

* * * * *